United States Patent [19]
Weng et al.

[11] Patent Number: 5,575,286
[45] Date of Patent: Nov. 19, 1996

[54] METHOD AND APPARATUS FOR GENERATING LARGE COMPOUND ULTRASOUND IMAGE

[75] Inventors: Lee Weng; Arun P. Tirumalai, both of Issaquah, Wash.

[73] Assignee: Siemens Medical Systems, Inc., Iselin, N.J.

[21] Appl. No.: 414,978

[22] Filed: Mar. 31, 1995

[51] Int. Cl.⁶ .................................................. A61B 8/00
[52] U.S. Cl. .................... 128/653.1; 128/660.08
[58] Field of Search .................. 128/653.1, 653.2, 128/654, 659, 660.01, 660.07, 660.08

[56]         References Cited

U.S. PATENT DOCUMENTS

| | | | |
|---|---|---|---|
| 4,431,007 | 2/1984 | Amazeen et al. | 73/626 |
| 4,580,219 | 4/1986 | Pelc et al. | 364/414 |
| 5,045,939 | 9/1991 | Okayama et al. | 358/140 |
| 5,051,826 | 9/1991 | Ishii et al. | 358/140 |
| 5,107,837 | 4/1992 | Ophir et al. | 128/660.01 |
| 5,178,147 | 1/1993 | Ophir et al. | 128/660.01 |
| 5,247,937 | 9/1993 | Ophir et al. | 128/661.03 |
| 5,257,626 | 11/1993 | Pelc et al. | 128/653.2 |
| 5,262,856 | 11/1993 | Lippman et al. | 358/136 |
| 5,293,870 | 3/1994 | Ophir et al. | 128/660.01 |
| 5,305,104 | 4/1994 | Jensen et al. | 348/473 |
| 5,353,354 | 10/1994 | Keller et al. | 382/6 |
| 5,474,070 | 12/1995 | Ophir et al. | 128/660.01 |

OTHER PUBLICATIONS

Yo Egusa et al., "An Electronic Video Camera Image Stabilizer Operated on Fuzzy Theory", *IEEE (journal unknown)*, pp. 851–858, 1992.

Kenya Uomori et al., "Automatic Image Stabilizing System By Full–Digital Signal Processing", *IEEE Transactions on Consumer Electronics*, vol. 36, No. 3, pp. 510–519, Aug. 1990.

An Electronic Video Camera Image Stabilizer Operated On Fuzzy Theory, by Yo Egusa et al., 1991 IEEE (0–7803–0236–Feb. 1992), pp. 851–858.

*Primary Examiner*—Francis Jaworski

[57]         ABSTRACT

An image registration method and apparatus is provided in which consecutive ultrasonic image frames are correlated in order to derive transducer motion information. Since ultrasonic images from real-time scanning operations are highly correlated from one frame to another, the individual images can be divided into several smaller sub-image regions and a very fast and robust image motion detection algorithm utilized to measure the sub-image motion. This algorithm uses a fast adaptive coarse/fine minimum-sum-absolute-difference (MSAD) search strategy to compute an initial estimation of the local motion vectors. The initial estimation is combined with two measurement parameters by use of a fuzzy logic technique to derive a final estimation of the local motion vectors. The final local motion vectors are applied to a least-squares (L-S) process in order to estimate global image motion. Finally, a fast display technique generates compound images based on the derived global image motion.

24 Claims, 6 Drawing Sheets

METHOD AND APPARATUS FOR GENERATING LARGE COMPOUND ULTRASOUND IMAGE

BACKGROUND OF THE INVENTION

1. Field of the Invention

This invention relates to ultrasonic diagnostic imaging, and more particularly, to an ultrasonic imaging system that produces a large compound image by correlating movement between consecutive image frames.

2. Description of Related Art

Ultrasonic imaging techniques are commonly used to produce two-dimensional diagnostic images of internal features of an object, such as a human anatomy. A diagnostic ultrasonic imaging system for medical use forms images of internal tissues of a human body by electrically exciting an acoustic transducer element or an array of acoustic transducer elements to generate short ultrasonic pulses that travel into the body. The ultrasonic pulses produce echoes as they reflect off of body tissues that appear as discontinuities or impedance changes to the propagating ultrasonic pulses. These echoes return to the transducer, and are converted back into electrical signals that are amplified and decoded to produce a cross-sectional image of the tissues. These ultrasonic imaging systems are of significant importance to the medical field by providing physicians with real-time, high resolution images of the internal features of a human anatomy without resort to more invasive exploratory techniques, such as surgery.

The acoustic transducer which radiates the ultrasonic pulses typically comprises a piezoelectric element or matrix of piezoelectric elements. As known in the art, a piezoelectric element deforms upon application of an electrical signal to produce the ultrasonic pulses. In a similar manner, the received echoes cause the piezoelectric element to deform and generate the corresponding electrical signal. The acoustic transducer is often packaged within a handheld device that allows the physician substantial freedom to easily manipulate the transducer over a desired area of interest. The transducer can then be electrically connected via a cable to a central control device that generates and processes the electrical signals. In turn, the control device transmits the image information to a real-time viewing device, such as a video display terminal. The image information may also be stored so that other physicians may view the diagnostic images at a later date.

The individual images produced by such ultrasonic imaging systems comprise discrete frames, with each such frame having a field of view limited by the relatively narrow region traversed by the ultrasonic pulses. As the transducer is manipulated along the body surface to obtain images of an adjacent region in the anatomy, each previous image is replaced on the viewing device by a new image defined by the limited field of view of the transducer. While a skilled physician can usually interpret the discrete frames in order to obtain a clear mental picture of the entire region traversed by the transducer, the discrete frames cannot be easily tiled together to produce a single, contiguous image. This can represent a significant drawback of conventional ultrasonic imaging systems, since it is not always possible for the physician to fully appreciate the overall condition of the body by consideration of the discrete frames alone. In some extreme cases, important information concerning the condition of the body tissues can be overlooked with serious potential consequences for the patient.

Previously, it has been demonstrated that a real-time compound ultrasonic image could be generated by use of so-called compound B-scanners. These B-scanners utilize a transducer mounted on an arm assembly that constrains the transducer to move along a single plane or axis. Either the arm assembly or the transducer element itself can be provided with sensing devices that track the precise position of the transducer. This positional information could then be utilized to register each of the discrete image frames together into a single composite image. An example of a compound B-scanner utilizing angular sensing devices on an arm assembly is disclosed in U.S. Pat. No. 4,431,007, to Amazeen et al., for REFERENCED REAL-TIME ULTRASONIC IMAGE DISPLAY. Despite this potential improvement in the art, conventional compound B-scanners are awkward and inflexible to operate due primarily to the relatively bulky mechanical arm assembly. Moreover, the sensing devices add significant complexity and cost to the ultrasonic imaging system. It should be apparent that the application of such prior art techniques to modern handheld ultrasonic transducers would be completely impractical in view of these significant drawbacks.

Thus, a critical need exists for a method to combine each of the discrete frames produced by an ultrasonic imaging system into a single image. The method should be compatible with modern handheld ultrasonic transducers without encumbering the handheld transducers with position sensing devices that increase the cost, weight and complexity of such imaging systems.

SUMMARY OF THE INVENTION

This application provides a method and apparatus for generating a large compound ultrasonic image. The method and apparatus utilizes image registration to eliminate the need for positional sensing devices altogether. In the image registration method and apparatus, consecutive moving image frames are correlated in order to derive the transducer motion information for compound image generation.

In particular, the method and apparatus recognizes that ultrasonic images from real-time scanning operations are highly correlated from one frame to another. Based on this recognition, the individual images are divided into several smaller sub-image regions, and a very fast and robust image motion detection algorithm is utilized to measure the sub-image motion. This algorithm uses a fast adaptive coarse/fine minimum-sum-absolute-difference (MSAD) search strategy to compute an initial estimation of the local motion vectors. The initial estimation is combined with two measurement parameters by use of a fuzzy logic technique to derive a final estimation of the local motion vectors. The final local motion vectors are applied to a least-squares (L-S) process in order to estimate global image motion. Finally, a fast display technique generates compound images based on the derived global image motion.

DETAILED DESCRIPTION

This invention satisfies the critical need for a method and apparatus to combine each of the discrete image frames produced by an ultrasonic imaging system into a single composite image. In the image registration method and apparatus of this invention, consecutive image frames are correlated in order to derive the transducer motion information for compound imaging. Significantly, the motion information is derived without encumbering the handheld transducer with position sensing devices that would otherwise increase the cost, weight and complexity of such ultrasonic imaging systems. In the detailed description that follows, like element numerals are used to describe like elements illustrated in one or more of the figures.

Figure 1:
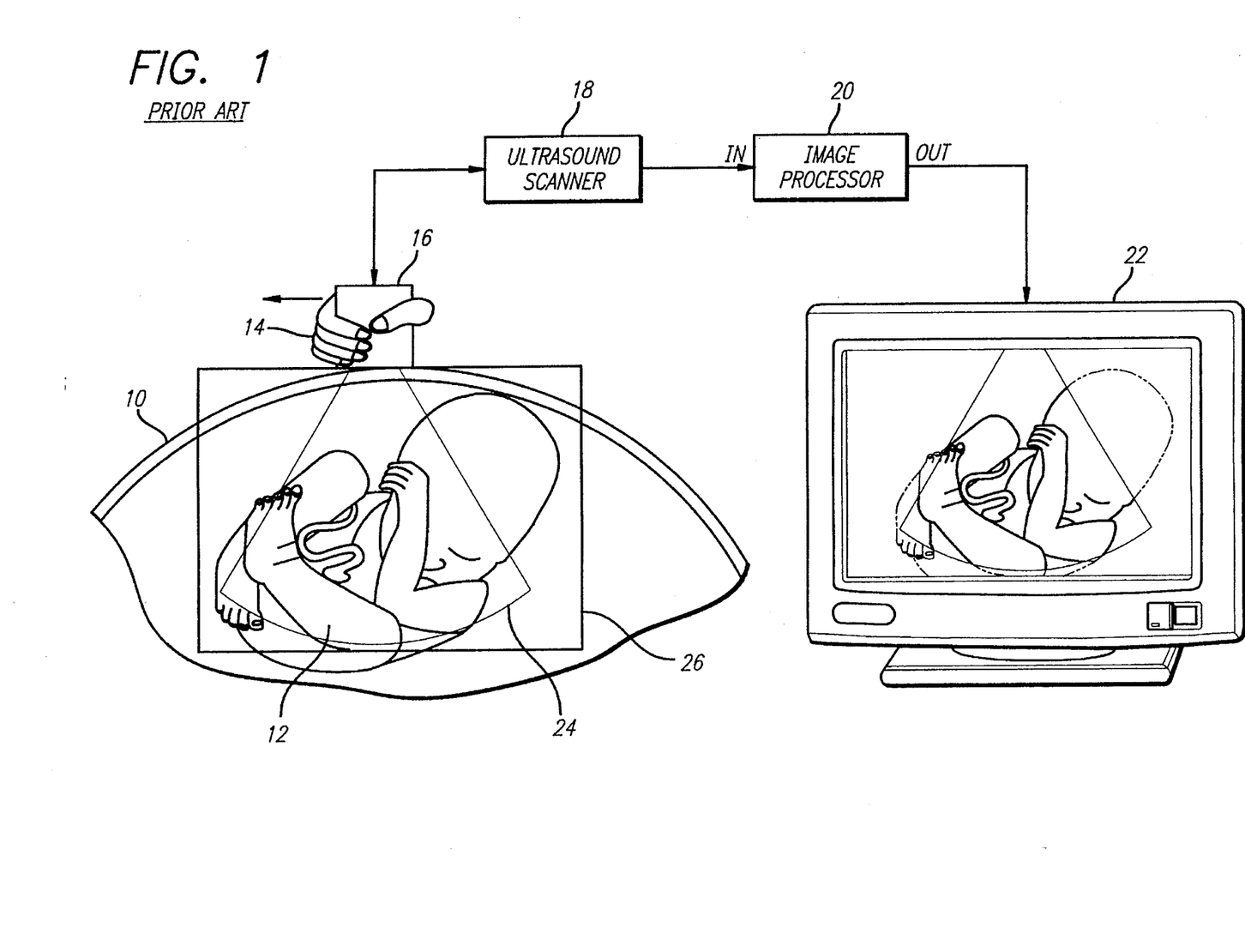
FIG. 1 is a partial perspective view of an ultrasonic imaging system adapted for real-time display of an exemplary fetal anatomy within a clinical environment.

Referring first to FIG. 1, a prior art ultrasonic imaging system adapted for real-time display within a clinical environment is illustrated. A patient 10 carrying a fetus 12 is lying in a supine position to permit a physician or other technician 14 to perform an ultrasonic imaging operation. The imaging system comprises a scanhead 16 coupled to an ultrasound scanner 18. To perform the imaging operation, the physician 14 draws the scanhead 16 along the patient's skin surface in a direction which is parallel with the ultrasonic scan plane. An acoustically conductive lubricating agent may be applied to the skin prior to bringing the scanhead 16 into contact with the skin so as to improve acoustic coupling between the scanhead and the patient.

The scanhead 16 includes an ultrasonic transducer disposed at a surface thereof, comprising a piezoelectric element or matrix of individual piezoelectric elements. The ultrasound scanner 18 provides electrical signals to the scanhead 16 that cause it to generate ultrasonic pulses. The ultrasonic pulses 24 propagate in the scan plane through the skin of the patient 10 and echo off of the anatomical features of the fetus 12. The echoes return through the skin to the scanhead 16, which converts the echoes back into electrical signals received by the ultrasound scanner 18. The received electrical signals are then transmitted from the ultrasound scanner 18 to an image processor 20. The image processor 20 decodes the electrical signals into a two-dimensional, cross-sectional image that is displayed on the video display terminal 22. The image information may also be electronically stored in a memory medium, including a permanent storage medium such as a disk or tape drive, a temporary storage medium such as a solid state memory, or can be printed to a hard copy image such as a photograph.

The ultrasonic image displayed on the video display terminal 22 (or stored by use of the various other storage media described above) comprises only the information representative of the relatively narrow region traversed by the ultrasonic pulses 24. As illustrated in FIG. 1, only a portion of the anatomical features of the fetus 12 are displayed on the video display terminal 22. The region outside the sector of the ultrasonic pulses 24 (illustrated in phantom in FIG. 1) actually appears blank on the display device 22. As noted above, it would be very desirable to provide a large compound image, such as a single image that includes the entire image region 26.

Figure 2:
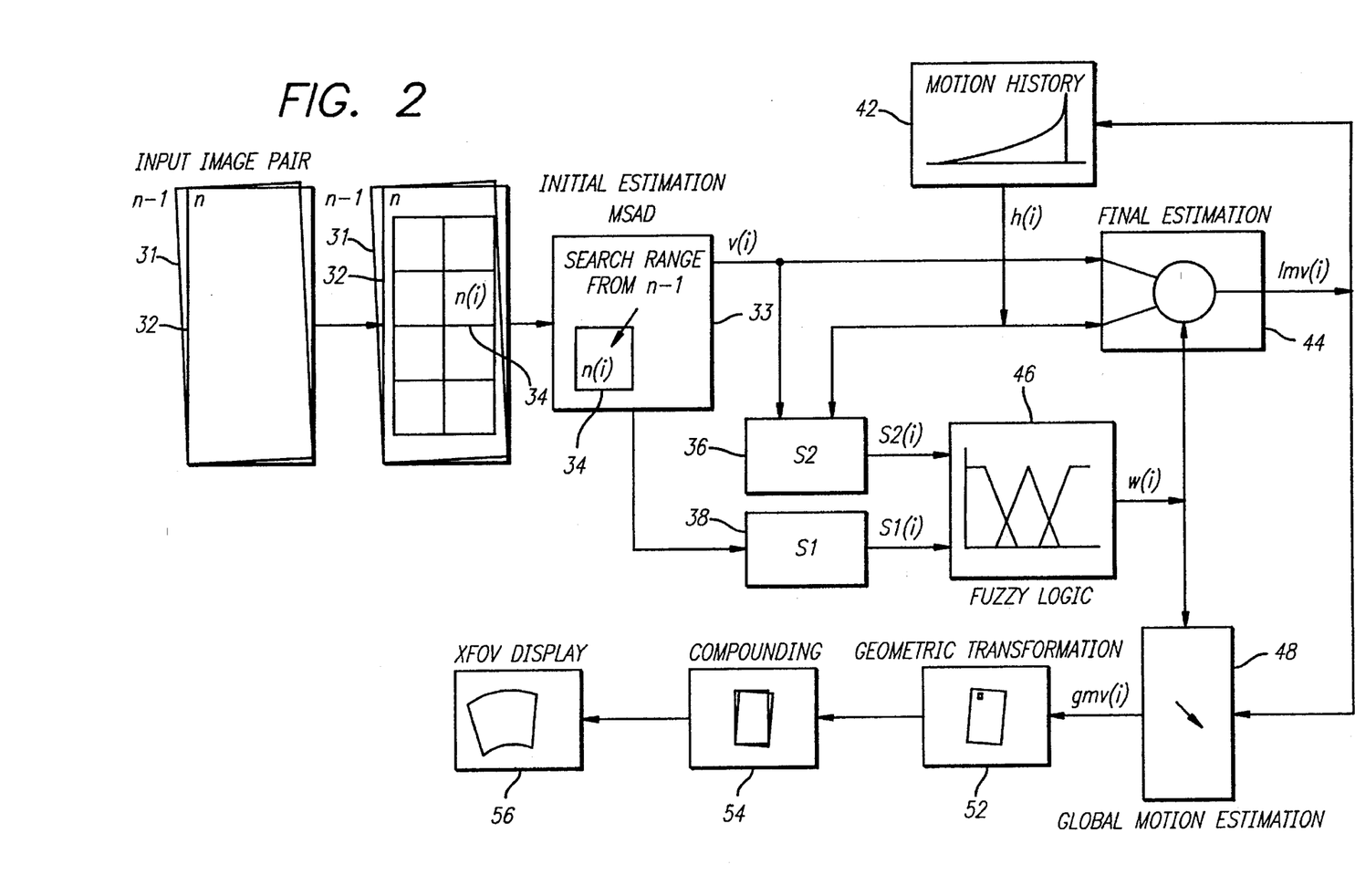
FIG. 2 is a block diagram illustrating an image registration method in accordance with this invention.

Referring now to FIG. 2, a block diagram of an image registration method in accordance with this invention is illustrated. Two consecutive image frames 31, 32 are denoted as frame n-1 (the previous frame) and frame n (the current frame), respectively. The previous image frame n-1 is treated as a reference image. The current image frame n acquired by moving the transducer 16 of FIG. 1 along the skin surface is compared with the previous image frame n-1 to estimate motion of the transducer. In order to estimate image motion from frame n-1 to frame n, frame n is divided into a plurality of sub-frame regions 34, and the local motion of each of the sub-frame regions is estimated. For I total blocks, the i'th block of frame n is defined as n(i).

The particular size and number of the blocks 34 are selected by consideration of various factors. The block size should approximate the size of the particular image features. For example, image features such as tissue boundaries and blood vessels would require a relatively small block size. Nevertheless, such a small block size would not be suitable for estimation of motion because the small block size decorrelates very rapidly with relatively large magnitudes of motion. Moreover, the small block size would not be stable for in-vivo images where small scale tissue motion exists. At the same time, if the block size is too large, there will be too few blocks per image frame for motion estimation and the motion estimation will be unstable. Further, a large block size may introduce an image rotation error into the local motion estimation where the block is incorrectly assumed to have a translation component but no rotation component.

In a preferred embodiment of the invention, a block size of approximately 48×48 pixels is deemed acceptable for motion estimation in view of these factors in relation to an image frame size of about 200×400 pixels. A minimum block size of 32×32 pixels could also be utilized in relation to a smaller image size. These block sizes result in a block number I between approximately eight and twenty in order to yield the best results.

Figure 3:
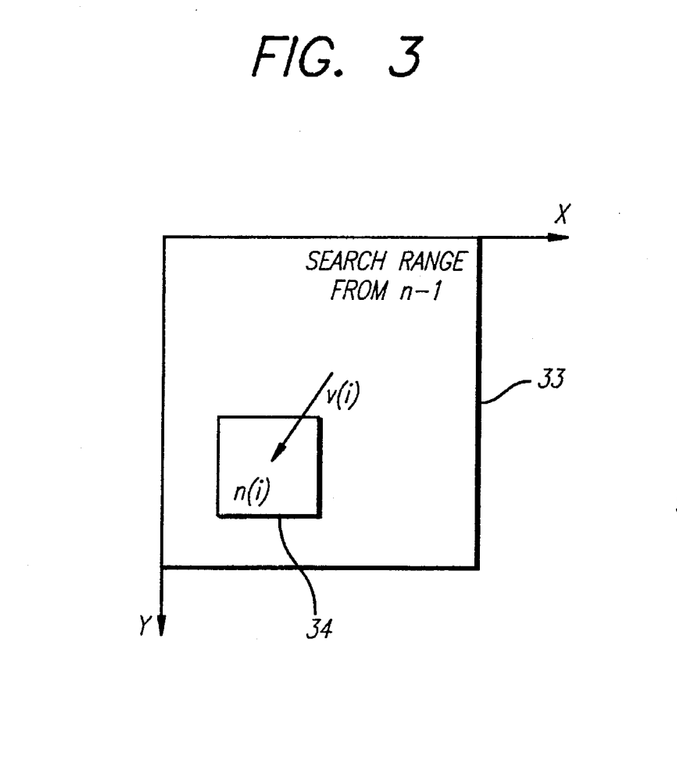
FIG. 3 is a block diagram illustrating a minimum-sum-absolute-difference search of the image registration method.

As illustrated in FIG. 3, local motion of each block n(i) of image n is estimated by moving the block n(i) (such as exemplary block 34) around on the n-1 image frame to find the best match. The search region size 33 on the n-1 image frame is less than the total area of the frame 31, and should relate to the expected image motion speed and image frame rate. For example, a large search region size 33 should be used when the transducer speed is high and also when the image frame rate is low. In a preferred embodiment, a search region size of 32 pixels in each of the four searching directions is adequate for use with an input image frame rate selected at 7.5 frame/second (computing one out of every four video frames), resulting in a search region size of 64×64 pixels.

Figure 5:
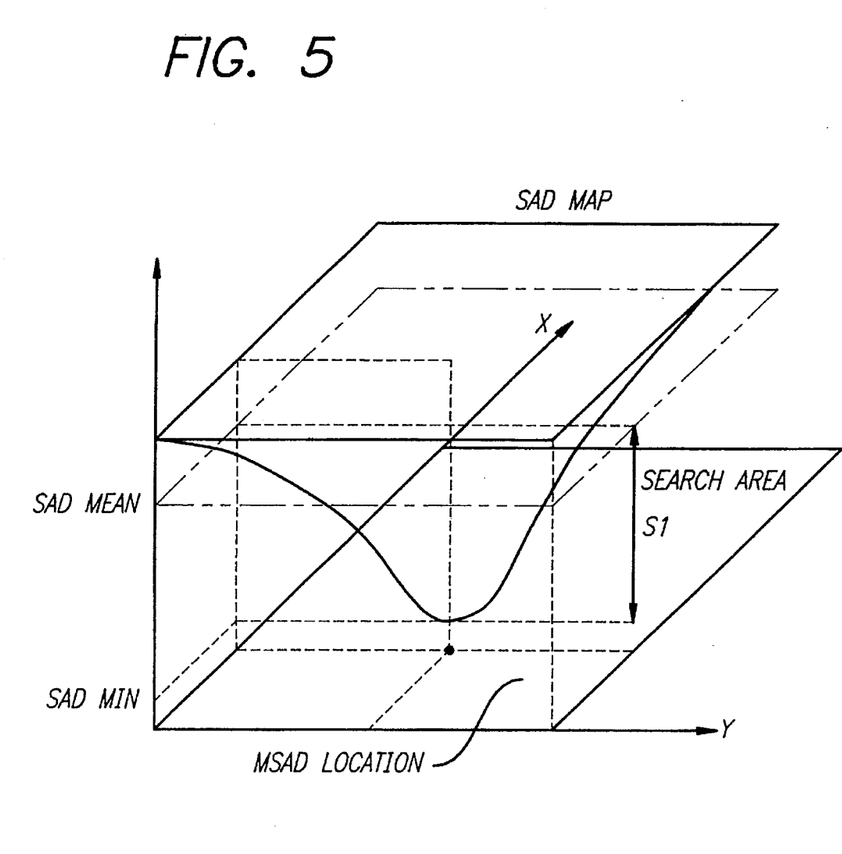
FIG. 5 is a three-dimensional graph illustrating derivation of a quality factor for the minimum-sum-absolute-difference search.

The "best match" is determined by use of a minimum-sum-absolute-difference technique (MSAD) to match the n(i) block 34 with the search region 33 of frame n-1. The sum-absolute-difference (SAD) is the sum of absolute differences between corresponding pixel values between each block 34 and the search region 33. The "best match" between the block 34 and the search region 33 occurs where the SAD value is at a minimum. FIG. 5 illustrates a SAD map having values that extend in the X and Y directions. The generally uniform SAD map contains a valley where the SAD values dip below the mean, representing the location of the MSAD. The MSAD technique is used to derive a first estimation of local motion vector v(i) having a direction and magnitude indicating how the block n(i) translated from the n-1 image frame to the n image frame. The direction of the local motion vector v(i) is denoted by the arrow of FIG. 3.

It should be apparent that calculating the MSAD could be a very slow computing process if the number of blocks is large, the block size is large, and the search region is large. For example, a frame n having sixteen blocks 34 with a 48×48 pixel block size and a search region of 64×64 pixels would require about 300,000,000 separate additions/subtractions and about 65,000 comparisons to complete a single MSAD computation. Even with the relatively high speed of conventional processors, this would still encompass too much computation to accommodate real-time application. Accordingly, various search techniques are utilized in order to reduce the magnitude of the MSAD computation.

Figure 4:
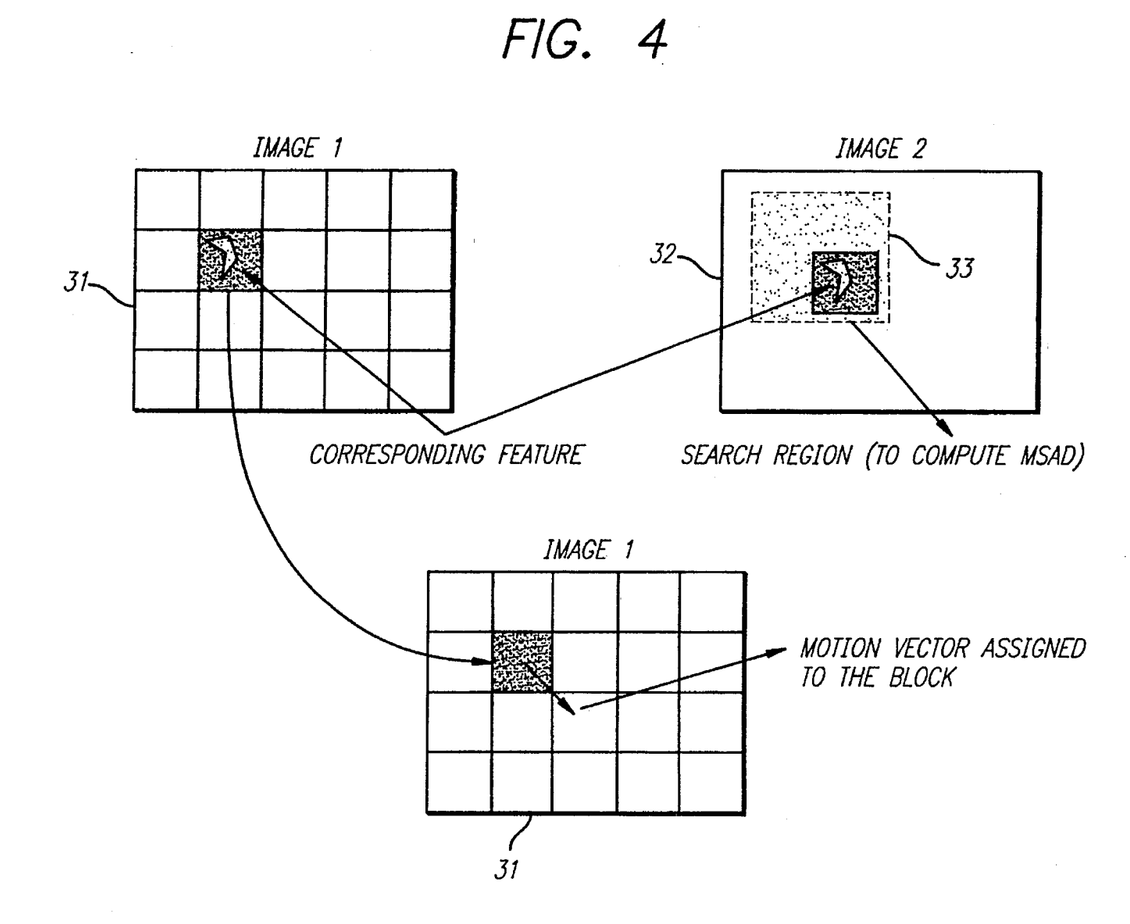
FIG. 4 is a block diagram illustrating an alternative embodiment of the minimum-sum-absolute-difference search.

One such technique for calculating the MSAD utilizes a conventional MPEG encoder. MPEG, or Moving Picture Expert Group, is an industry accepted data compression standard for digitizing graphical information. MPEG encoders are commercially available that can be used to perform a rough estimate of MSAD location based on historical movement of the image. A "best match" is sought between an image characteristic within a block 34 and a search region by searching within a local neighborhood comprising a finite dimensional range, such as within ten pixels in the X and Y directions relative to the image characteristic. In FIG. 4, the location of the MSAD is identified by application of the MPEG encoder, and a local motion vector assigned to the block 34. A drawback of the use of an MPEG encoder is that it results in a high incidence of inaccurate local motion vectors, which must be filtered out.

The accuracy of the local motion vector determination can be further improved by consideration of certain unique constraints of compound ultrasonic imaging. Motion in the Y direction (vertical) from one frame to another is almost always smaller than the motion in the X direction (horizontal), because the ultrasonic transducer 16 generally moves only along the patient body contour. This transducer motion can be characterized as being more of a horizontal extension than an up/down folding. Further, the transducer motion is most likely to be in one direction and continuous; sudden reversals in motion direction are not very likely. It has been found from a large number of experiments that MSAD maps are often fairly smooth and continuous even for blocks which have a lot of noise and lack of image features.

In view of these constraints, a fast adaptive coarse/fine MSAD search strategy can be devised that significantly reduces the total amount of computation. The search strategy requires that the search range in the X direction be larger than that in the Y direction, and the search range and direction should be adaptive to the overall motion history. For example, if the history shows the image motion is in +X direction, it is very likely the subsequent frame will also move in the same direction. Because the MSAD map is smooth and continuous, a coarse search can be performed first to reduce the search region 33 to a smaller area, followed by a fine search within the smaller area. Because motion in the Y direction is usually very small (and usually zero), the two-dimensional MSAD search can be reduced to two one-dimensional searches in the X and Y directions, respectively. The first search should be conducted in the X direction to quickly narrow down the search region, followed by subsequent alternating one-dimensional searches in both the X and Y directions to quickly find the MSAD location. Points which have been searched during the coarse search or have been searched in the other direction could be skipped during the fine search. Based on the above search strategy, in most cases the location of the MSAD can be identified after one coarse and one medium search in the X direction, one coarse search in the Y direction and one small two-dimensional fine search in both directions. For the same example given above, the total number of computations can be reduced to 2,600,000 additions/subtractions and 560 comparisons; representing a reduction of the total number of computations by roughly 115 times.

Under the influence of image noise, tissue motion and other image artifacts, the first MSAD motion estimation is not always very reliable. Accordingly, two measures of the quality and reliability of the first local motion vector estimation v(i) are devised, termed S1(i) and S2(i). Referring to FIG. 5, S1(i) is a quality factor of MSAD, and measures the difference between the value of MSAD and mean SAD. MSAD quality increases with the value of S1(i), i.e., the deeper the SAD valley, the better MSAD quality. When strong image noise exists, or when there is a lack of image features, the SAD map will become more flat so that S1(i) becomes smaller. In that case, the estimation of v(i) becomes less reliable.

Figure 6:
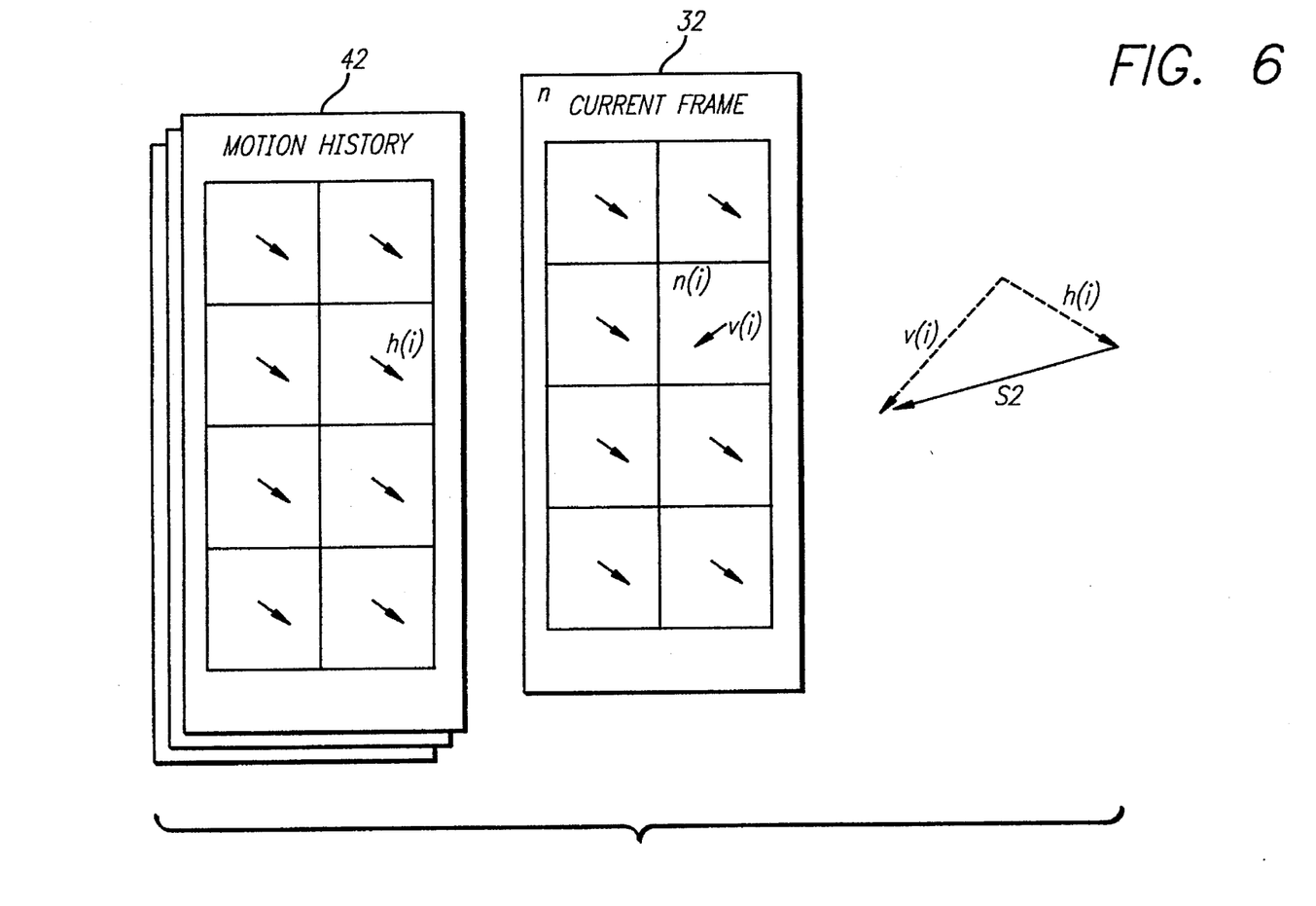
FIG. 6 is a block diagram illustrating derivation of a local vector deviation factor for the minimum-sum-absolute-difference search.

Referring to FIG. 6, the second parameter S2 (i) measures how much v(i) deviates from its past history. The motion history 42 of the i'th block, h(i) (also shown in FIG. 2), is the recursively weighted averaging of previous final local motion vector outputs of the i'th block. S2(i) is the vector difference between v(i) and h(i). Generally, image motion is fairly smooth and consistent for both experienced and unexperienced ultrasound operators. If one value of v(i) has a very different direction and magnitude as compared with its history, it is very likely that this estimation is under the influence of noise or local tissue motion and does not accurately reflect true image local motion. In this case the v(i) estimation is not very reliable. Thus, a large value of S2(i) indicates that the estimated v(i) is less reliable.

While the above estimation quality control concept is easy to understand, in practice it is difficult to implement since image changes caused by transducer motion can be rather complex. Accordingly, the quality and reliability of the motion estimate can be efficiently quantized by use of fuzzy logic. Referring back to FIG. 2, a fuzzy logic control block 46 receives S1(i) and S2(i) as inputs, combines them using fuzzy rules (described below), and produces a single numerical output w(i) which represents a degree of accuracy of v(i). The numerical output w(i) ranges from zero to one, with the estimation accuracy of v(i) increasing as w(i) approaches one.

Figure 7A:
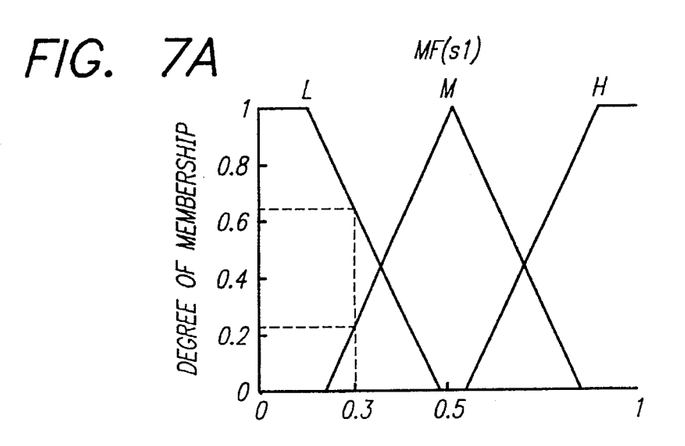
FIGS. 7A through 7D are graphs illustrating fuzzy logic membership functions for the quality factor and the deviation factor to derive a control value and a single numerical output.
Figure 7B:
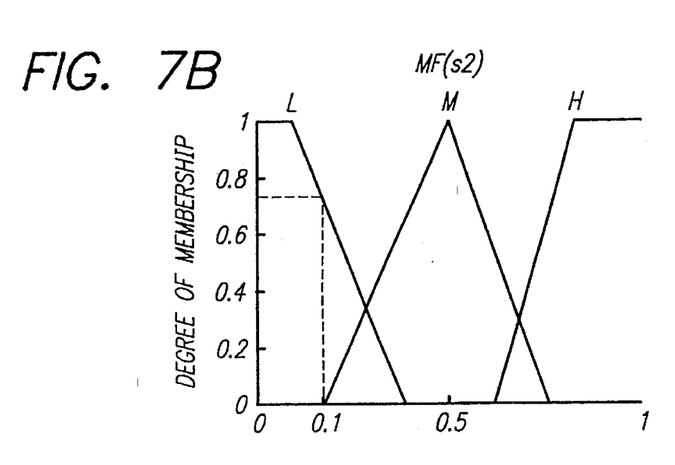
Figure 7C:
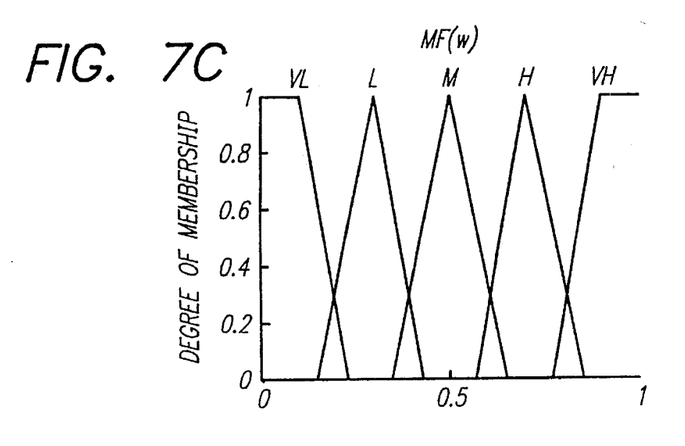

The inputs S1(i) and S2(i) are first "fuzzified" into the linguistic expressions, or labels, "high", "medium" and "low". Output w(i) also has its fuzzy expression as "very high", "high", "medium", "low" and "very low". Membership functions of S1(i), S2(i) and w(i) are defined from a large number of experimental results, and are illustrated at FIGS. 7A through 7C, respectively. The membership function of S1(i) is graphically illustrated at FIG. 7A as comprising three regions labeled as L (low), M (medium) and H (high). The regions overlap to a certain extent; specifically, the L and M regions overlap, and the M and H regions overlap. The horizontal axis of the membership function graph defines the measured value of S1(i), and the vertical axis defines the degree of membership of the measured value within the defined label.

The membership function of S2(i) is graphically illustrated at FIG. 7B, and is constructed similar to the membership function of S1(i). Similarly, the membership function of w(i) is graphically illustrated at FIG. 7C, and is constructed similar to the membership functions of S1(i) and S2(i), though it includes five overlapping regions labeled as VL (very low), L (low), M (medium), H (high), and VH (very high).

Seven fuzzy rules are used to define the relationship between S1(i), S2(i) and w(i). These fuzzy rules include:

(1) If S1(i) is low (L) AND S2(i) is also low (L), then w(i) is medium (M);

(2) If S1(i) is medium (M) AND S2(i) is low (L), then w(i) is high (H);

(3) If S1(i) is high (H) AND S2(i) is low (L), then w(i) is very high (VH);

(4) If S1(i) is low (L) AND S2(i) is medium (M), the w(i) is low (L);

(5) If S1(i) is medium (M) AND S2(i) is also medium (M), then w(i) is medium (M);

(6) If S1(i) is high (H) AND S2(i) is medium (M), then w(i) is high (H); and (7) If S2(i) is high (H), then w(i) is very low (VL).

The fuzzy rules are applied in parallel to determine the truth of the rules. For example, assume that measured values of S1(i) and S2(i) are 0.3 and 0.1, respectively. In FIG. 7A, a measured value of 0.3 relates to degrees of membership of approximately 0.65 in the L label and approximately 0.25 in the M label. In FIG. 7B, a measured value of 0.1 relates to a degree of membership of approximately 0.75 in the L label only. As a result, only the first two fuzzy rules are true, though they yield inconsistent results in that the first fuzzy rule concludes w(i) is medium and the second fuzzy rule concludes that w(i) is high. The output w(i) must be converted back to a numerical value, and the inconsistent results must be reconciled.

Figure 7D:
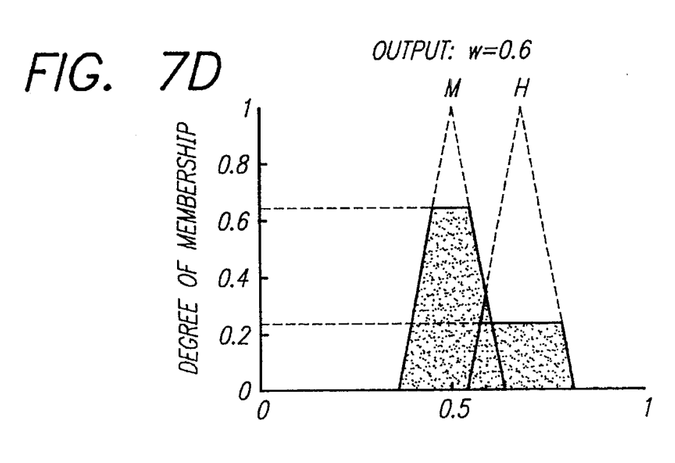

Under the first fuzzy rule, the low value of S1(i) is combined using a logical AND with the low value of S2(i) to provide the medium value of w(i). Under the logical AND operation, the minimum value of the truth of the expressions is taken as the truth level of the rule. In other words, the 0.65 degree of membership of S1(i) is less than the 0.75 degree of membership of S2(i), and is thus taken as the truth level for the first fuzzy rule. Similarly, under the second fuzzy rule, the medium value of S1(i) is combined using a logical AND with the low value of S2(i) to provide the high value of w(i). The 0.25 degree of membership of S1(i) is less than the 0.75 degree of membership of S2(i), and is thus taken as the truth level for the second fuzzy rule. The M and H labels of the w(i) membership function are then truncated at the truth levels defined by the fuzzy rules, as illustrated graphically in FIG. 7D.

Finally, a centroid defuzzification technique is used to convert the fuzzy output back to a numerical number w(i). Using this technique, an estimate of the center of gravity is provided for the entire region determined to be true (illustrated as the shaded region of FIG. 7D). From FIG. 7D, the center of gravity of the shaded region is approximately 0.6, providing a numerical value for w(i).

After the reliability parameter w(i) is obtained, the next step is to use w(i) to improve the local motion estimation v(i). If w(i) is large, v(i) is used directly as the final local motion vector 1 mv(i). In contrast, if w(i) is very small, the average frame motion history h(i) is used as the estimated 1 mv(i), since the motion history is more likely to be a better estimation than the less reliable v(i). If w(i) is neither very large nor very small, it is used as a weighing factor to average v(i) and h(i). For instance, if w(i)=0.6, as in the above example, then 1 mv(i)=0.6*v(i)+(1−0.6)*h(i).

The motion history h(i) is also updated recursively by weighting 1 mv(i). The weight is selected to be between zero and one; a larger weight value makes the very recent motion estimation contribute more to the history h(i). For example, if the weight is 0.5, then h(i)=0.5*1 mv(i)+(1−0.5)*h(i).

Once all of the local motion vector outputs 1 mv(i) are estimated for the n'th frame, the outputs are combined together at 48 of FIG. 2 to estimate the frame global motion vector, gmv(i). Minimum least-squares (L-S) error parameter fitting is used to combine the motion vector outputs, using three optimization parameters including frame translation (Xn, Yn) and rotation en. The weighted L-S gives the local motion vector v(i) which has a larger w(i) more weight than those having smaller w(i). This way, the more reliable local motion vectors v(i) contribute more heavily to the optimization process. The geometrically corrected frames are combined together at 54 of FIG. 2 to form a compound image. Three techniques can be applied to combine the corrected frames, including "image growing" which only puts new pixel data in the non-overlapping part to the compound image buffer, "recursive spatial compounding" which recursively averages the new image frame with existing compound image, and "ramp compounding" which gives weight ramps for both new image frame and existing compound image in the overlapping area. This latter technique successfully reduces compound image local discontinuity caused by motion jitters. Finally, the compound image is displayed on a video display terminal 56 or other such device, providing the full image represented in phantom on the terminal 22 of FIG. 1, described above.

It should be apparent that the above method and apparatus for generating a compound image is applicable to both real-time imaging and re-generation of recorded image information. In application, a physician may use a conventional ultrasonic imaging system to produce image frames that are recorded onto a permanent storage medium, such as tape. Subsequently, the image frames could be processed into a compound image for later viewing by the physician by bringing the recorded image frame data to a viewing station. The viewing station would then process the image frame data by use of the method described above to generate a compound image. It should also be apparent that the method and apparatus of this application are not limited to processing of ultrasonic images, but would be equally applicable to other imaging modalities, such as radar or photographic imaging.

What is claimed is:

1. A method for providing a compound image, comprising the steps of:

generating a plurality of substantially adjacent image frames of an interrogation region of a patient's body;

dividing individual ones of the image frames into a plurality of sub-image regions;

estimating local motion vectors of the respective sub-image regions between consecutive ones of the image frames;

estimating global image motion based on the estimated local motion vectors; and displaying a compound image based on the estimated global image motion.

2. The method of claim 1, wherein the step of dividing the individual image frames into a plurality of sub-image regions further comprises the step of dividing the individual image frames into a range of approximately eight to twenty sub-image regions.

3. The method of claim 1, wherein the estimating steps are performed concurrently with the generating step so that a real-time compound image is provided in the displaying step.

4. A method for providing a compound image from a plurality of individual image frames, comprising the steps of:

dividing the individual image frames into a plurality of sub-image regions;

estimating local motion vectors of the respective sub-image regions between consecutive ones of the individual image frames;

estimating global image motion based on the estimated local motion vectors; and displaying a compound image based on the estimated global image motion;

wherein the step of estimating local motion vectors further comprises the steps of:

calculating an initial estimation of the local motion vectors using a fast adaptive coarse/fine minimum-sum-absolute-difference (MSAD) search; and deriving a final estimation of the local motion vectors from the initial estimation of the local motion vectors by use of a fuzzy logic technique.

5. The method of claim 4, wherein the step of deriving a final estimation further comprises the step of defining a first quality factor of the MSAD by measuring the difference between the value of MSAD and mean sum-absolute-difference (SAD).

6. The method of claim 5, wherein the step of deriving a final estimation further comprises the step of defining a second quality factor of MSAD by measuring deviation of the initial estimation of the local motion vector from an historical measurement of the local motion vector.

7. The method of claim 6, wherein the step of deriving a final estimation further comprises the step of defining membership functions for the first and second quality factors.

8. The method of claim 7, wherein the step of deriving a final estimation further comprises the step of determining a membership value for the first and second quality factors.

9. The method of claim 8, wherein the step of deriving a final estimation further comprises the step of combining the membership values for the first and second quality factors in accordance with predefined fuzzy rules to generate an output value.

10. The method of claim 9, wherein the step of deriving a final estimation further comprises the step of averaging the initial estimation of the local motion vectors with the historical estimation of the local motion vectors using the output value as a weight.

11. The method of claim 4, wherein the step of calculating an initial estimation of the local motion vectors further comprises the steps of conducting a one-dimensional search in a first axial direction and at least one additional one-dimensional search in a second axial direction perpendicular to said first axial direction.

12. The method of claim 4, wherein the step of calculating an initial estimation of the local motion vectors further comprises the steps of defining a search region having an area greater than an associated one of the sub-image regions, the one-dimensional searches being conducted within the search region.

13. A method for providing a compound image from a plurality of individual image frames, comprising the steps of:

dividing the individual image frames into a plurality of sub-image regions;

estimating local motion vectors of the respective sub-image regions between consecutive ones of the individual image frames;

estimating global image motion based on the estimated local motion vectors; and displaying a compound image based on the estimated global image motion;

wherein the step of estimating global image motion further comprises the step of applying the estimated local motion vectors to a least-squares (L-S) process.

14. An apparatus for providing a compound image, comprising:

an ultrasonic scanner providing a plurality of individual ultrasonic image frames;

means for dividing the individual image frames into a plurality of sub-image regions;

means for estimating local motion vectors of the respective sub-image regions between consecutive ones of the individual image frames by use of a minimum-sum-absolute-difference search;

means for estimating global image motion based on the estimated local motion vectors; and means for displaying a compound image based on the estimated global image motion.

15. The apparatus of claim 14, wherein the means for estimating local motion vectors further comprises:

means for calculating an initial estimation of the local motion vectors using a fast adaptive coarse/fine minimum-sum-absolute-difference (MSAD) search; and means for deriving a final estimation of the local motion vectors from the initial estimation of the local motion vectors by use of a fuzzy logic technique.

16. The apparatus of claim 15, wherein the deriving means further comprises means for defining a first quality factor of the MSAD by measuring the difference between the value of MSAD and mean sum-absolute-difference (SAD).

17. The apparatus of claim 16, wherein the deriving means further comprises means for defining a second quality factor of MSAD by measuring deviation of the initial estimation of the local motion vector from an historical measurement of the local motion vector.

18. The apparatus of claim 17, wherein the deriving means further comprises means for defining membership functions for the first and second quality factors.

19. The apparatus of claim 18, wherein the deriving means further comprises means for determining a membership value for the first and second quality factors.

20. The apparatus of claim 19, wherein the deriving means further comprises means for combining the membership values for the first and second quality factors in accordance with predefined fuzzy rules to generate an output value.

21. The apparatus of claim 20, wherein the deriving means further comprises means for averaging the initial estimation of the local motion vectors with the historical estimation of the local motion vectors using the output value as a weight.

22. An apparatus for providing a compound ultrasonic image, comprising:

an ultrasonic scanner providing a plurality of substantially adjacent ultrasonic image frames, said image frames each respectively having a plurality of sub-image regions;

means for estimating local motion of the respective sub-image regions between consecutive ones of the image frames by calculating an initial estimation of the local motion and deriving a final estimation of the local motion from the initial estimation;

means for estimating global image motion based on the estimated local motion; and means for displaying a compound image based on the estimated global image motion.

23. The apparatus of claim 22, wherein said means for estimating local image motion further comprises a fast adaptive coarse/fine minimum-sum-absolute-difference (MSAD) search.

24. The apparatus of claim 22, wherein both said means for estimating local and global image motion are adapted to operate concurrently with said ultrasonic scanner to permit said displaying means to provide a real-time compound image.

* * * * *